US010863762B2

(12) United States Patent
Wicking et al.

(10) Patent No.: US 10,863,762 B2
(45) Date of Patent: Dec. 15, 2020

(54) MINERAL ENRICHED NATURAL SUPPLEMENTS

(71) Applicant: CURA GLOBAL HEALTH (BVI) LIMITED, Road Town Tortola (VG)

(72) Inventors: J. Bruce Wicking, Ames, IA (US); Yilin Bian, Ames, IA (US); Anbin Pu, Ames, IA (US); Kathleen Mary Petersen, Ames, IA (US)

(73) Assignee: CURA GLOBAL HEALTH (BVI) LIMITED, Tortola (VG)

( * ) Notice: Subject to any disclaimer, the term of this patent is extended or adjusted under 35 U.S.C. 154(b) by 228 days.

(21) Appl. No.: 15/552,052

(22) PCT Filed: Feb. 25, 2016

(86) PCT No.: PCT/AU2016/000057
§ 371 (c)(1),
(2) Date: Aug. 18, 2017

(87) PCT Pub. No.: WO2016/134406
PCT Pub. Date: Sep. 1, 2016

(65) Prior Publication Data
US 2018/0035704 A1 Feb. 8, 2018

Related U.S. Application Data

(60) Provisional application No. 62/121,321, filed on Feb. 26, 2015.

(51) Int. Cl.
*A23L 33/16* (2016.01)
*A23L 31/00* (2016.01)
(Continued)

(52) U.S. Cl.
CPC ............... *A23L 31/00* (2016.08); *A23K 10/16* (2016.05); *A23K 20/24* (2016.05); *A23K 20/30* (2016.05);
(Continued)

(58) Field of Classification Search
CPC .......... A23V 2200/30; A23V 2250/208; A23V 2250/156; A23V 2250/206;
(Continued)

(56) References Cited

U.S. PATENT DOCUMENTS 6,270,809 B1 * 8/2001 Ensley .................. A23K 20/30
424/600
2006/0280753 A1 12/2006 McNeary
(Continued)

FOREIGN PATENT DOCUMENTS

CN 1227869 9/1999
CN 1632128 6/2005
(Continued)

OTHER PUBLICATIONS

Int'l Preliminary Report on Patentability (IPRP) issued in App. No. PCT/AU16/00057 (2017).
(Continued)

*Primary Examiner* — Hong T Yoo
(74) *Attorney, Agent, or Firm* — Barnes & Thornburg LLP; Alice O. Martin (57) ABSTRACT

The technology relates to nutritional supplements containing one or more minerals. In particular the technology relates to nutritional supplements comprising filamentous fungal biomass and one or more minerals selected from zinc, magnesium, selenium, chromium, copper and manganese, and a process to make the nutritional supplements.

13 Claims, 2 Drawing Sheets

(51) Int. Cl.
  *A23K 10/16* (2016.01)
  *A23K 20/24* (2016.01)
  *A23K 20/20* (2016.01)
  *A23L 33/00* (2016.01)
  *A61K 36/06* (2006.01)
  *A61K 36/062* (2006.01)

(52) U.S. Cl.
  CPC .............. *A23L 33/00* (2016.08); *A23L 33/16* (2016.08); *A61K 36/06* (2013.01); *A61K 36/062* (2013.01); *A23V 2002/00* (2013.01)

(58) Field of Classification Search
  CPC ...... A23V 2250/21; A61K 8/97; A61K 36/06; A61K 36/062; A61K 33/26; A61K 33/24; A61K 35/78; C12N 1/14; C12N 9/242; A23L 31/00; A23L 33/105; A23L 1/30; A23L 1/28; A23L 1/304; A23L 1/0035; A23L 2/52; A23L 1/0017; A23L 1/0029
  See application file for complete search history.

(56) References Cited

U.S. PATENT DOCUMENTS

2007/0190209 A1* 8/2007 Sinnott ............... A61K 36/31
                                                              426/72
2015/0250839 A1* 9/2015 Wicking ............. A61K 33/26
                                                              424/93.5

FOREIGN PATENT DOCUMENTS

| | | |
|---|---|---|
| CN | 1961747 | 5/2007 |
| CN | 103011948 | 4/2013 |
| CN | 103109676 | 5/2013 |
| CN | 103858663 | 6/2014 |
| RU | 2422043 | 6/2011 |
| WO | WO 1998/054948 | 12/1998 |
| WO | WO 2006/012739 | 2/2006 |
| WO | WO 2014/040122 | 3/2014 |

OTHER PUBLICATIONS

Sharma, "Pathogenecity of *Aspergillus niger* in Plants," Cibtech Journal of Microbiology, 1(1): 47-51 (Apr.-Jun. 2012).

* cited by examiner

MINERAL ENRICHED NATURAL SUPPLEMENTS

CROSS REFERENCE TO RELATED APPLICATIONS

This application is a U.S. nationalization under 35 U.S.C. § 371 of International Application No. PCT/AU2016/000057, filed 25 Feb. 2016, which claims the benefit of priority under 35 U.S.C. § 119(e) to U.S. Provisional Patent Application No. 62/121,321, filed 26 Feb. 2015. The disclosures set forth in the referenced applications are incorporated herein by reference in their entireties.

TECHNICAL FIELD

The technology relates to natural supplements containing fungal biomass and one or minerals such as zinc, magnesium, selenium, chromium, copper and manganese.

BACKGROUND

The importance of trace elements in human nutrition and health has been recognized for many years. In a 1996 report by the World Health Organization (WHO), the trace elements were grouped as:

A. Essential—iodine (I), zinc (Zn), selenium (Se), copper (Cu), molybdenum (Mo) and chromium (Cr);

B. Probably essential—manganese (Mn), silicon (Si), nickel (Ni), boron (B) and vanadium (V).

Iodine has been widely fortified in table salt but other elements have not been commonly addressed. For example, zinc deficiency in the developing world that may lead to adverse health consequences and restricted child growth and development.

The trace element selenium is found in many enzymes such as glutathione peroxidase, thioredoxin reductase and deiodinases. These enzymes are recognized for the roles in antioxidation, muscle function and tumor prevention (Mehdi, Y. et al. 2013. Selenium in the environment, metabolism and involvement in body functions. Molecules 18:3292-3311).

The trace element chromium has been considered as an essential nutrient required for sugar and fat metabolism. Insufficient dietary intake of chromium leads to signs and symptoms that are similar to those observed for diabetes and cardiovascular diseases (Anderson, R A at al, 1997. Elevated intakes of supplemental chromium improve glucose and insulin variables of people with type II diabetes. Diabetes 46:1786-1791). Supplemental chromium given to people with impaired glucose tolerance or diabetes could improve their blood glucose, insulin, and lipid profiles (Cefalu, W T, and Hu F B. 2004. Role of chromium in human health and in diabetes. Diabetes Care. 27(11):2741-2751).

The trace element copper is usually obtained in sufficient quantities through regular diet. But people with anemia may also be copper deficient. Copper as part of the class of antioxidants such as zinc which can improve immune function (Maggini S. et al., 2007. Selected vitamins and trace elements support immune function by strengthening epithelial barriers and cellular and humoral immune responses. Br J Nutr. 98: S29-35).

The trace element manganese is also important to humans for the involvement in many enzymes activities (Watts, D L. 1990. The nutritional relationships of manganese. J. Ortho Med. 5(4):219-222). Both deficiency and excess of manganese have been studied and shown to be detrimental.

Magnesium is a major mineral in the human skeleton but has not received the same attention as calcium. It is as important as, if not more important than, calcium and phosphorus (Fawcett, W J, et al 1999. Magnesium: physiology and pharmacology. Bri J Anaesthesia 83 (2): 302-320). Magnesium is also a co-factor for many enzymes. The prevalence of cardiovascular disease has been in part attributed to magnesium deficiency which is common in patients.

Most of the mineral supplements in the market place are inorganic compounds such as, zinc, manganese or copper sulfate, zinc oxide, zinc or chromium picolinate, sodium selenite, selemethionine, magnesium sulfate, and magnesium citrate, etc. However, such compounds have limited use in the fortification of staple foods such as flour and rice. There has been development of the biofortification of staple crops but there is a long development time ahead. The use of microorganisms to shorten the bioconversion of inorganic minerals to organic has been conducted on yeast. Although yeast products enriched separately with zinc, iron, chromium, selenium or magnesium are being evaluated as mineral supplements, the bioavailability associated with these products are not conclusive.

The daily recommended dosage for zinc, selenium, chromium, copper, manganese and magnesium are set out in Table 1 (Food and Nutrition Board, Institute of Medicine, National Academies. Recommended dietary allowances and adequate intakes, elements. 2014.)

TABLE 1

Dietary reference intakes (DRIs): Recommended dietary allowances and adequate intakes

| Group | Zinc (mg/day) | Selenium (μg/day) | Chromium (μg/day) | Copper (mg/day) | Manganese (mg/day) | Magnesium (mg/day) |
| --- | --- | --- | --- | --- | --- | --- |
| Children 4-8 | 5 | 5 | 15 | 0.4 | 1.5 | 130 |
| Males 14+ | 11 | 55 | 35 | 0.9-1.3 | 2 | 400-420 |
| Females 14+ | 11 | 55 | 24 | 0.9-1.3 | 2 | 310-360 |
| Pregnancy 19+ | 11 | 60 | n/a | n/a | n/a | 350-400 |

The present applicant has developed a process using *Aspergillus oryzae* (*A. oryzae*) or *Aspergillus niger* (*A. niger*) to produce an iron-enriched fungal cell mass (WO 2014/040122). Up to 4% iron could be incorporated into the cell mass of the fungi which is much higher than in yeast.

The present inventors have developed nutritional supplements containing minerals that do not include raised levels of iron from fungi.

SUMMARY

Nutritional supplements containing fungal biomass and zinc, magnesium, selenium, chromium, copper and/or manganese and methods for forming nutritional supplements containing zinc, magnesium, selenium, chromium, copper and/or manganese are disclosed.

In one aspect, there is provided a nutritional supplement comprising: filamentous fungal biomass having elevated levels of a mineral selected from the group consisting of zinc, magnesium, selenium, chromium, copper, manganese and combinations thereof.

In one embodiment the nutritional supplement does not contain significant levels of iron.

In one embodiment the nutritional supplement has levels of iron less than 200 mg/kg.

In one embodiment the fungal biomass is from *Aspergillus oryzae* (*A. oryzae*) or *Aspergillus niger* (*A. niger*).

In one embodiment the nutritional supplement contains zinc.

In one embodiment the nutritional supplement contains magnesium.

In one embodiment the nutritional supplement contains selenium.

In one embodiment the nutritional supplement contains chromium.

In one embodiment the nutritional supplement contains copper.

In one embodiment the nutritional supplement contains manganese.

In one embodiment the nutritional supplement contains a combination of two or more of zinc, magnesium and selenium.

In one embodiment the nutritional supplement contains zinc, magnesium and selenium.

In one embodiment the nutritional supplement contains a combination of two or more of zinc, magnesium, selenium, chromium, copper and manganese.

In one embodiment the nutritional supplement contains zinc, magnesium, selenium, chromium, copper and manganese.

In one embodiment the nutritional supplement contains from about 1 to about 60000 mg/kg of at least one mineral selected from zinc, magnesium, selenium, chromium, copper and manganese.

In one embodiment the elevated level of zinc is at least about 500 mg/kg, the elevated level of magnesium is at least about 500 mg/kg, the elevated level of selenium is at least about 1 mg/kg, the elevated level of chromium is at least about 4 mg/kg, the elevated level of copper is at least about 60 mg/kg, and the elevated level of manganese is at least about 60 mg/kg.

In one embodiment the elevated level of zinc is at least about 2500 mg/kg, the elevated level of magnesium is at least about 2500 mg/kg, the elevated level of selenium is at least about 5 mg/kg, the elevated level of chromium is at least about 20 mg/kg, the elevated level of copper is at least about 300 mg/kg, and the elevated level of manganese is at least about 300 mg/kg.

In one embodiment the elevated level of zinc is at least about 5000 mg/kg, the elevated level of magnesium is at least about 5000 mg/kg, the elevated level of selenium is at least about 10 mg/kg, the elevated level of chromium is at least about 40 mg/kg, the elevated level of copper is at least about 600 mg/kg, and the elevated level of manganese is at least about 600 mg/kg.

In one embodiment the nutritional supplement contains zinc from about 500 to about 40000 mg/kg, magnesium from about 500 to 40000 mg/kg, and/or selenium from about 1 to 3500 mg/kg, chromium from about 4 to 8000 mg/kg; copper from about 60 to 20000 mg/kg, and/or manganese of about 60 to 20000 mg/kg.

In one embodiment the nutritional supplement contains zinc from about 2500 to about 40000 mg/kg, magnesium from about 2500 to 40000 mg/kg, selenium from about 5 to 3500 mg/kg, chromium from about 20 to 8000 mg/kg; copper from about 300 to 20000 mg/kg, and/or manganese of about 300 to 20000 mg/kg.

In one embodiment the nutritional supplement contains zinc from about 5000 to about 40000 mg/kg, magnesium from about 5000 to 40000 mg/kg, selenium from about 10 to 3500 mg/kg, chromium from about 40 to 8000 mg/kg, copper from about 600 to 20000 mg/kg, and/or manganese of about 600 to 20000 mg/kg.

The nutritional supplement may include diluents or other co-ingredients such as calcium, potassium and phosphorus and inorganic salts thereof.

The nutritional supplement may be formulated as a powder, solution, drink, capsule, tablet, or caplet.

An advantage of the nutritional supplement is that it contains natural organic zinc, magnesium, selenium, chromium, copper and/or manganese formed during culture of the filamentous fungi on agricultural by-products or food processing by-products. The nutritional supplement may be produced or formulated to further contain phytase and other enzymes naturally produced by the filamentous fungi.

The nutritional supplement may contain additional inorganic zinc, magnesium, selenium salts, chromium salts, copper salts and/or manganese salts or other high zinc, magnesium, selenium, chromium, copper and/or manganese compounds added during growth of the filamentous fungi. Examples include, zinc chloride, zinc sulphate, magnesium chloride, magnesium sulphate, sodium selenite, chromium chloride, copper and manganese.

The nutritional supplement may be formulated for human or animal use.

In another aspect there is provided a nutritional product comprising the nutritional supplement according to the present technology.

The nutritional product may be a food product, processed food product, drink, sports drink, energy drink, energy bar, breakfast cereal, dairy product, animal feed, pet food, and the like.

The powdered form of product can also be added to food and used as a food fortification ingredient. The fortification of food includes, but is not limited to condiments, salt, baby formula, and flours of wheat, corn and beans.

The present invention also relates to the growth of filamentous fungi, such as *Aspergillus oryzae* (*A. oryzae*) or *niger* (*A. niger*) to produce mineral rich natural supplements containing one or more of zinc, magnesium, selenium, chromium, copper and manganese.

The filamentous fungi may be cultured in media in part formulated with either food grade agriculture or food processing by-products to produce the mineral rich natural supplements.

In another aspect, there is provided a process for forming a nutritional supplement containing elevated levels of a mineral, the process comprising:

culturing filamentous fungi in an agricultural by-product or a food processing by-product to accumulate a mineral selected from the group consisting of zinc, magnesium, selenium, chromium, copper, manganese and combinations thereof in the filamentous fungi; and harvesting the filamentous fungi to obtain a nutritional supplement containing fungal biomass having elevated levels of a mineral selected from the group consisting of zinc, magnesium, selenium, chromium, copper, manganese and combinations thereof.

In an embodiment the filamentous fungi is selected from *Aspergillus oryzae* (*A. oryzae*) or *Aspergillus niger* (*A. niger*).

The agricultural by-product can be from waste derived from corn, wheat, sugar beet, cane sugar, soybean, whey from agriculture production. Examples of such products are sugar cane and beet pulps, soybean hull, soybean process whey, wheat hull, corn steeping liquid and soybean whey.

In some embodiments the food processing by-product is selected from corn steeping liquor, soybean whey, sugar cane and beet molasses, soybean hull and wheat bran, wheat hull and food process by-product.

Additional growth media can be provided to the agricultural by-product or the food processing by-product to assist growth and accumulation of zinc, magnesium, selenium, chromium, copper and/or manganese by the filamentous fungi during culture.

In one embodiment the one or more minerals are converted to an organic form in the fungal cell mass.

The zinc, magnesium, selenium, chromium, copper and/or manganese may be obtained from the agricultural by-product or the food processing by-product or provided salts of zinc, magnesium, selenium chromium, copper and/or manganese added to the culture medium for accumulation by the filamentous fungi.

Additional inorganic salts and other high zinc, magnesium, selenium, chromium, copper and/or manganese compounds including zinc salts, such as zinc sulfate, magnesium salts, such as magnesium sulfate or magnesium chloride, selenium salts such as sodium selenite, chromium salts such as chromium chloride, copper salts such as copper sulphate, manganese salts such as manganese sulphate but not limited to these salts maybe added during growth of the filamentous fungi to further increase zinc, magnesium, selenium, chromium, copper and/or manganese content of the nutritional supplement.

Inorganic salts of zinc, magnesium, selenium, chromium, copper and/or manganese can be added to the fungal culture media at concentration of at least about 5 mg of salt per liter of media. In some embodiments, about 50 to 1500 mg of salt per liter of media can be used.

The nutritional supplement may further include other minerals such as calcium and potassium. To achieve further mineral supplementation, calcium carbonate, potassium phosphate and potassium chloride may be added to the culture.

In one embodiment the nutritional supplement does not contain significant levels of iron.

In one embodiment the nutritional supplement contains less than 200 mg/kg iron.

Additional culture media or nutrients may be provided to assist in growth of the filamentous fungi. Examples include yeast extract, hydrolyzed plant based protein, ammonium salts, urea, potassium phosphorus, copper salt and corn steeping liquor.

The filamentous fungi may be cultured in any suitable environment such as fermentation vessels used in both solid and liquid fermentations.

Culture of the filamentous fungi may be carried out at room temperature or elevated temperatures such as 25 to 35° C.

The filamentous fungi can be harvested by any suitable means. Examples include filtration, such as filter press, belt press; centrifugation, such as decanter, drying, such as rotary drier, steam drier and vacuum drier. The drying temperature is typically lower than about 95° C. to reduce any unwanted heat damage of the product.

The harvested filamentous fungi may be further processed to form the nutritional supplement containing zinc, magnesium and/or selenium. Further processing may include separating, crushing, grinding, fractionation, extraction, washing with cold and hot water to remove excess salts, or mild acid with pH of 2 or alkaline wash with pH of 9-10 to remove other soluble compounds.

The zinc and/or magnesium content may be higher than 40000 mg/kg but the fungal biomass yield may be reduced and this may not be economical in practice. Higher than 3500 mg/kg of selenium is achievable but may also reduce the biomass yield in the process.

The nutritional supplement containing zinc, magnesium, selenium, chromium, copper and/or manganese may include diluents or other co-ingredients such as calcium, potassium, phosphorous and inorganic salts thereof.

The nutritional supplement may contain additional inorganic zinc, magnesium selenium, chromium, copper, manganese salts or other high zinc, magnesium, selenium chromium, copper and/or manganese compounds added during growth of the filamentous fungi.

In another aspect, there is provided a process for forming a nutritional supplement containing elevated levels of a mineral, the process comprising:

providing a culture medium containing an agricultural by-product or a food processing by-product and salts or compounds of a mineral selected from the group consisting of zinc, magnesium, selenium, chromium, copper, manganese and combinations thereof;

culturing filamentous fungi in the culture medium to accumulate a mineral selected from the group consisting of zinc, magnesium, selenium, chromium, copper, manganese and combinations thereof in the filamentous fungi; and harvesting the filamentous fungi to obtain a nutritional supplement containing fungal biomass having elevated levels of a mineral selected from the group consisting of zinc, magnesium, selenium, chromium, copper, manganese, and combinations thereof.

The salts or compounds include zinc salts, such as zinc sulfate, magnesium salts, such as magnesium sulfate or magnesium chloride.

Selenium can be added to the culture medium in the form of sodium selenite.

Chromium can be added to the culture medium in the form of chromium chloride.

Copper can be added to the culture medium in the form of copper sulphate.

Manganese can be added to the culture medium in the form of manganese sulphate.

In a further aspect, the technology relates to a nutritional supplement containing zinc, magnesium, selenium, chromium, copper and/or manganese produced by the process described herein.

In a further aspect, the technology relates to a method for the treatment or prevention of one or more of zinc, magnesium, selenium chromium, copper, manganese deficiency, the method comprising administering a therapeutically effective amount of the nutritional supplement described herein.

In a further aspect, the technology relates to use of the nutritional supplement described herein for the manufacture of a medicament for the treatment or prevention of one or more of zinc, magnesium, selenium, chromium, copper, manganese deficiency.

In a further aspect, the technology relates to a method for the treatment or prevention of a condition characterized by zinc, magnesium, selenium, chromium, copper and or manganese deficiency, the method comprising administering a therapeutically effective amount of a nutritional supplement described herein to a subject in need thereof.

In a further aspect, the technology relates to use of a nutritional supplement described herein for the manufacture of a medicament for the treatment or prevention of a condition characterized by zinc, magnesium, selenium, chromium, copper, manganese deficiency.

In conditions characterized by zinc, magnesium, selenium, chromium, copper, manganese deficiency may include poor immune system function, slow growth, fatigue and impaired glucose tolerance, intolerance to cold, anxiety and muscle weakness, slowed growth combined with iron deficiency, and dermatitis and nervous irritability.

In a further aspect, the technology relates to a nutritional supplement containing a mineral selected from the group consisting of zinc, magnesium, selenium, chromium, copper, manganese and combination thereof derived or obtained from filamentous fungi cultured in an agricultural by-product or a food processing by-product.

The present inventors have found that elevated levels of iron are not required to produce the nutritional supplement containing zinc, magnesium, selenium, chromium, copper and/or manganese.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present invention may be more clearly understood, preferred embodiments will be described with reference to the following drawings and examples.

DESCRIPTION OF EMBODIMENTS

Fungi

Fungi, including filamentous fungi, have the ability to further uptake relatively bio-unavailable minerals. For example, *A. oryzae* and *A. niger* have the ability to accumulate organic iron and other minerals from natural sources such as agricultural and food process wastes/by-products with the addition of high concentrations of inorganic minerals. Accordingly, in some embodiments of the present technology, the fungal biomass is filamentous fungal biomass, for example, *A. oryzae* and *A. niger* biomass.

Agricultural by-Product Selection and Pretreatment

There are many by-products produced from agricultural and food processing, but not all of them are naturally rich in minerals. Suitable agricultural by-products that could be used for the production of mineral enriched fungal products, include corn, wheat bran, rice bran, soybean hulls, rice hulls, molasses from sugar cane or beets, fruit juice processing pulp, potato skins, corn steeping liquors and soybean whey.

Even though many of the by-products are recognized as containing minerals, many are not approved or suitable for direct human consumption. Most minerals in grain by-products are bound by phytate and as a result the natural forms are not bioavailable to humans. For example, the use of phytase to improve iron bioavailability in many of these products is well understood but the daily human requirement is relatively too large for improving iron status. It has been found by the present inventors that selected fungal species can be used as a means to concentrate minerals into a natural cell form. With the addition of inorganic salts of zinc, magnesium, selenium, chromium, manganese or copper during the growth of fungi, the inorganic mineral is converted to an organic form in the fungal cell mass. The mineral rich fungi can also be produced with synthetic media made up with carbon such as glucose, nitrogen source such as urea, phosphorus source such as potassium phosphate. The advantages of using the agricultural by-products are that these by-products also provide micronutrients and vitamins to the fungi. Agricultural by-products are normally both under-valued and under-utilized.

Before any by-product can be used in the production of the mineral-fungal product, testing is required for microbial spoilage, mycotoxins, pesticide residues and heavy metal contamination. For liquid raw materials, dilution may be necessary as the optimal total solids is 3-10% for liquid fermentation of fungal species, such as *A. oryzae* or *A. niger*. Dry raw materials may be ground, soaked or cooked to release natural minerals and reduce anti-fermentation factors. To maximize natural mineral release from raw materials, enzymes, such as cellulase, hemicellulase and phytase may be used during soaking and cooking of the by-products. Multiple raw materials may also be used at the same time depending upon availability and pricing.

Depending on the nutritional profile of the raw materials, other nutrients may be needed to supplement the growth media for an aerated fungal fermentation. These nutrients may include organic and inorganic nitrogen sources, phosphorous sources and/or micro minerals.

The agricultural by-product can be, but not limited to, from waste derived from corn, wheat, sugar beet, cane sugar, soybean processes. Examples of such products are sugar cane and beet pulps, wheat bran and hull, rice bran and hull, soybean hull, soybean process whey, corn steeping liquor and soybean whey.

In some embodiments the food processing by-product is selected from corn steeping liquor, soybean whey, sugar cane and beet molasses, soybean hull and wheat bran and wheat hull.

The present technology relates to the use of selected fungal species as the means to concentrate minerals into an organic form suitable for animal or human consumption.

Before any by-product can be used in the production of a nutritional supplement, testing is preferably carried out for microbial spoilage, mycotoxins and heavy metal contamination. For liquid raw materials, dilution may be necessary as the optimal total solids for liquid fermentation of fungal species, such as *Aspergillus oryzae* or *Aspergillus niger* is about 3-10%. Dry raw materials may be ground, soaked or cooked to release natural minerals and reduce anti-fermentation factors. To assist natural mineral release from raw materials, enzymes, such as cellulase, hemicellulase and phytase, may be used during soaking and cooking. Multiple raw materials may be used at the same time depending upon availability and pricing.

Process

Figure 1:
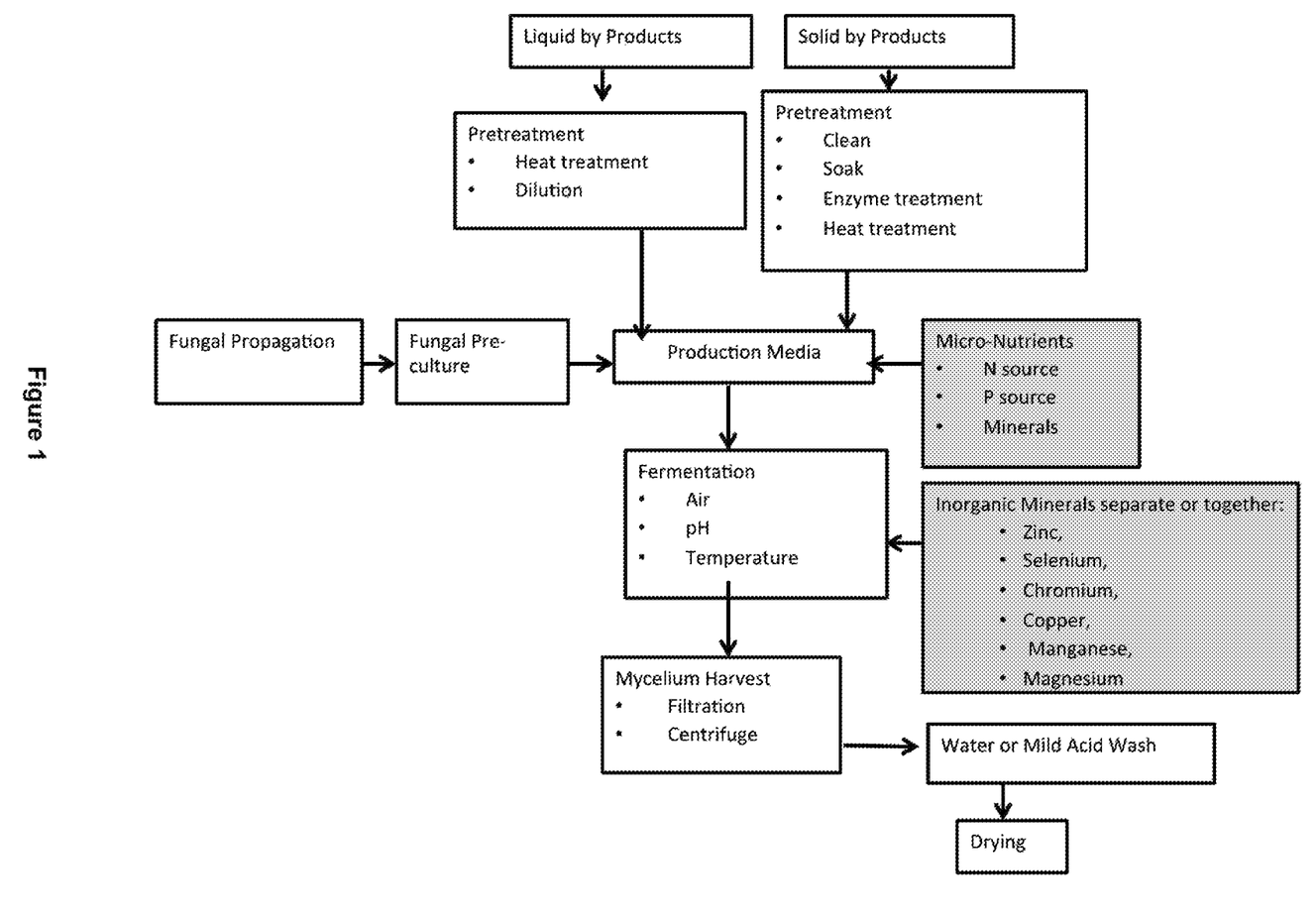
FIG. 1 shows basic steps in the production of natural mineral rich fungal biomass.

General steps of a preferred process using an agricultural by-product or a food processing by-product are set out in FIG. 1.

Fungal Strains

Strains of *Aspergillus oryzae* used were the same strains that are approved and employed commercially for soy sauce and miso manufacture, including *Aspergillus oryzae* 2355 and 40151 from Chinese Center of Industrial Culture Collection (CICC); *Aspergillus oryzae* 22787 from American Type Culture Collection (ATCC) and *Aspergillus niger* var. 2206 and 10557 for citric acid production from CICC and *Aspergillus niger* 66876 for phytase production from ATCC. Other strains of *A. oryzae* can be used in the technology.

Fungal Culture

Strains of *Aspergillus oryzae* and *Aspergillus niger* were cultured and maintained in media composed of ground whole corn, wheat bran, soybean hulls, molasses of beet, cane and fruits juice process by-product, and any other food process by-product consisting of starch, sugar and protein. Such raw materials can be pretreated by enzymes, including amylases, gluco-amylases, phytase and protease. Inorganic salts were added to the fungal culture media, such inorganic salts of zinc, selenium, magnesium, chromium, copper and/or manganese at concentration of at least about 5 mg of salt per liter of media. In some embodiments, about 50 to 1500 mg of salt per liter of media can be used.

Fungal spores were prepared by inoculating a solid media, such as cooked rice, soybean, and sorghum and the combination of them with moisture of 40-70%. In two to three weeks, the spores germinated and were ready to be collected. The fungal spores were collected into sterilized distill water. The pre-cultures fermenters were prepared with 1-10% volume of the final production fermenters. The media for the pre-cultures can be the same as the production media as described above. Incubation for 18 to 28 hours of pre-culture fermentation time is suitable to generate healthy pre-cultures after the spores were introduced into the pre-culture media. The pre-culture is added to the production fermenter and fungus is allowed to grow to produce the desired fungal mass containing zinc, selenium magnesium, copper, chromium and/or manganese.

Apparatus

Large scale fermentation can be carried out in any suitable fermentation vessel or apparatus. For the mineral enriched biomass production, the fermentation is preferably carried out under aerobic conditions for 48-72 hours. Sterilized or filtered air can be pumped into the fermenter at 0.5 to 1.0 vvm during the fermentation period to improve growth and yield. The culture is preferably agitated or stirred during fermentation. The combination of air, agitation and design of the fermentation vessel is well understood for commercial microbial culture.

Fungal Fermentation

Fermentation can be carried out for 48-72 hours or to reach maximum biomass at a temperature of 25-35° C. A temperature of 28-30° C. has been found to be suitable. It will be appreciated that incubation times and temperature may vary depending on the fungus type and strain used. In some embodiments, the temperature may be in the range of about 20° C. to about 40° C. For example, the temperature may be in the range of about 20° C. to about 30° C., about 25° C. to about 35° C., about 30° C. to about 40° C., or about 25° C. to about 30° C., e.g. about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

Depending on the nutritional profile of the raw materials, other nutrients may be needed to supplement the growth media for an aerated fungal fermentation. These nutrients may include organic and Inorganic carbon sources, nitrogen sources, phosphorous sources and micro minerals.

Production of Mineral Enriched Fungal Products

It should be noted that, direct supplementation of soluble inorganic salts in human diets can result in a cytotoxic reaction. Therefore, using fungi to uptake the inorganic mineral salts and transform to an organic form may reduce the side effects of the direct consumption of salts. Inorganic salts can be added during the fungal fermentation. The common choice of inorganic salts, depending on the final desired product, includes magnesium salts, such as magnesium sulfate or magnesium chloride, zinc salts, such as zinc sulfate and zinc chloride, selenium salt, such as sodium selenite, chromium salts such as chromium chloride, copper salts such as copper sulphate, and manganese salts such as manganese sulphate. The inorganic mineral is converted to an organic form by the fungi. To maximize the level of required mineral in the fungal product, a given mineral salt can be incrementally fed during the fermentation. The dosing of mineral salts depends on the type of salt used but the dosing level needs to not compromise the growth of fungi. After harvest, the fungal mycelium/biomass can be thoroughly washed to remove excess mineral salts. A mild acid, pH 3-4, wash can be effective in this regard.

Fungal Biomass Harvesting

Figure 2:
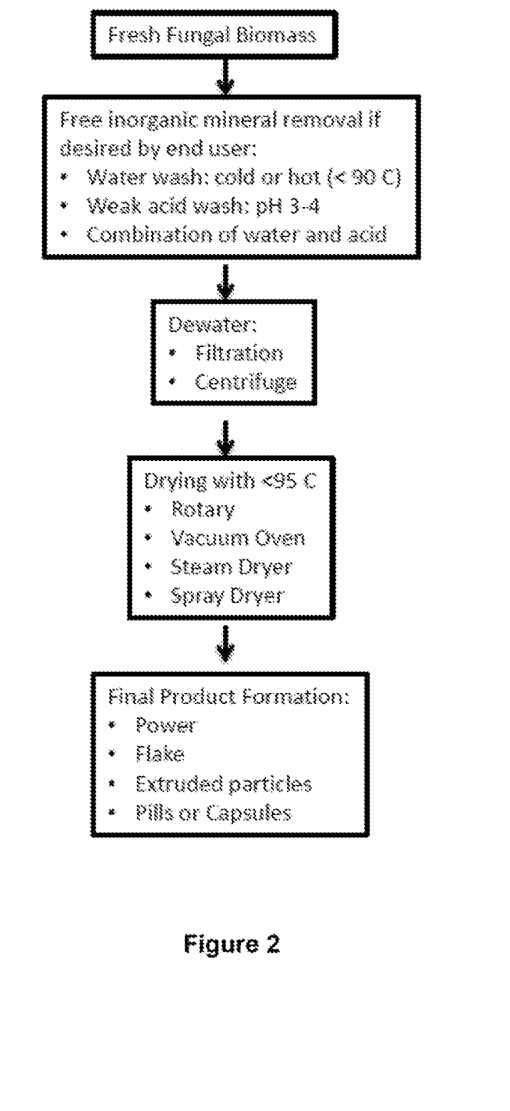
FIG. 2 shows summary of post-harvest process steps to produce the final natural mineral-rich products.

After fermentation, fungal biomass containing the mineral or minerals can be harvested by a dewatering machine such as a centrifuge, belt press etc. Washing with water and/or mild acid such as hydrochloric or citric acid 0.001 M to 0.01 M can be used to remove inorganic salt residues. The mineral enriched fungal product can then be dried at 60-95° C. using forced air, vacuum drying, etc (see FIG. 2). The final moisture content of the product is usually less than about 10% by weight. The final form of the product could be made according to the application requirement.

Supplements

The nutritional supplement may contain zinc in the range of about 10 to about 60000 mg/kg. For example, the nutritional supplement may contain zinc in the range of about 10 to about 60000 mg/kg, about 500 to about 40000 mg/kg, about 500 to about 4000 mg/kg, about 2000 to about 40000 mg/kg, or about 5000 to about 60000 mg/kg, e.g. 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 45000, 50000, 55000 or 60000 mg/kg zinc.

The nutritional supplement/ingredient may contain magnesium in the range of about 10 to about 60000 mg/kg. For example, the nutritional supplement may contain magnesium in the range of about 10 to about 40000 mg/kg, about 500 to about 40000 mg/kg, about 500 to about 4000 mg/kg, about 2000 to about 40000 mg/kg, or about 5000 to about 40000 mg/kg, e.g. 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 30000, 35000, 40000, 45000, 50000, 55000 or 60000 mg/kg magnesium.

The nutritional supplement may contain selenium in the range of about 1 to about 4000 mg/kg. For example, the nutritional supplement may contain selenium in the range of about 1 to about 4000 mg/kg, about 5 to about 4000 mg/kg, about 10 to about 4000 mg/kg, about 100 to about 4000 mg/kg, or about 1000 to about 4000 mg/kg, e.g. 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3800, 3700, 3800, 3900 or 4000 mg/kg selenium.

The nutritional supplement may contain chromium in the range of about 4 to 8000 mg/kg. For example, the nutritional supplement may contain chromium in the range of about 10 to about 8000 mg/kg, about 50 to about 8000 mg/kg, about 100 to about 8000 mg/kg, about 1000 to about 8000 mg/kg, or about 5000 to about 8000 mg/kg, e.g. 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4500, 5000, 5500, 6000, 6500, 7000, 7500 or 8000 mg/kg selenium.

The nutritional supplement may contain copper in the range of about 60 to 20000 mg/kg. For example, the nutritional supplement may contain copper in the range of about 300 to about 20000 mg/kg, about 600 to about 20000 mg/kg, about 1000 to about 20000 mg/kg, about 5000 to about 20000 mg/kg, or about 10000 to about 20000 mg/kg, or about 15000 to about 20000 mg/kg, e.g. 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000 mg/kg copper.

The nutritional supplement may contain manganese in the range of about 60 to 20000 mg/kg. For example, the nutritional supplement may contain manganese in the range of about 300 to about 20000 mg/kg, about 600 to about 20000 mg/kg, about 1000 to about 20000 mg/kg, about 5000 to about 20000 mg/kg, or about 10000 to about 20000 mg/kg, or about 15000 to about 20000 mg/kg, e.g. 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000 mg/kg manganese.

The nutritional supplement may include diluents or other co-ingredients such as calcium, potassium, phosphorus and inorganic salts thereof.

Formulation

The nutritional supplement may, for example, be formulated for oral delivery. Non-limiting examples of particular formulation types include tablets, capsules, caplets, powders, granules, ampoules, vials, ready-to-use solutions or suspensions, drinks, and lyophilized materials. The solid formulations such as the tablets or capsules may contain any number of suitable acceptable excipients or carriers. Food application may include powder, flake or extruded forms, or/and blended with other minerals, vitamins and food ingredients.

The nutritional supplement may be formulated for human or animal use.

The nutritional supplement according to the present technology can be used to form nutritional products. The nutritional product may be a food product, processed food product, drink, sports drink, energy drink, energy bar, breakfast cereal, dairy product, animal feed, pet food, and the like.

The powdered form of product can also be added to food and used as a food fortification ingredient. The fortification of food includes, but is not limited to condiments, salt, baby formula, and flours of wheat, corn and beans.

The nutritional supplement containing the elevated level of the mineral may be formulated as a powder, solution, drink, capsule, tablet, or caplet. The biomass can be processed to form powder, flake, and extruded forms which can be added to food and used as a food fortification ingredient. The fortification of food includes, but is not limited to condiments, salt, baby formula, breakfast cereals and flours of wheat, corn and beans.

An advantage of the nutritional supplement is that it contains natural organic minerals derived from fermentation of the by-products. The nutritional supplement may be formulated to further contain phytase and other enzymes naturally produced by the filamentous fungi.

The nutritional supplement can be formulated for human or animal use.

EXAMPLES

It has been found that *A. oryzae* and *A. niger* have the ability to accumulate organic minerals from natural sources such as agricultural and food process wastes/by-products with the addition of high concentrations of inorganic minerals.

Typical mineral concentrations in growth media are listed in Table 2 for the healthy growth of the fungi. It will be appreciated that the types of Mg, Zn and Se compounds are not limited to those listed in Table 2. The concentrations of minerals can be greatly increased for fungi such as *A. oryzae* and *A. niger* (Table 3) to produce a mineral enhanced fungal biomass that can be used as human supplements or food fortification.

The final form of each mineral enriched fungal biomass is in a solid form, but can also be re-solubilized by acid or alkaline to form a solution. Both the solid, such as powder, and the solution can be used as a mineral supplement alone or combined and/or added to food.

TABLE 2

Ranges of typical concentrations of mineral components (g/L) in fungal growth media

| Component | Range as Salt | Range as Element |
|---|---|---|
| $MgSO_4 \cdot 7H_2O$ | 0.25-3.0 | 0.025-0.295 |
| $CaCO_3$ | 5.0-17.0 | 2.0-6.8 |
| $ZnSO_4 \cdot 8H_2O$ | 0.1-1.0 | 0.02-0.2 |
| Selenium | none | none |
| Chromium | none | none |
| Copper | 0.003-0.01 | 0.000076-0.0025 |
| Manganese | 0.01-0.1 | 0.0032-0.032 |

TABLE 3

Amount of each inorganic mineral salt added separately during the fermentation of *A. oryzae* (g/L)

| Component | Range as Salt | Range as Element |
|---|---|---|
| $MgCl_2 \cdot 6H_2O$ | 2.08-4.16 | 0.25-0.5 |
| $ZnSO_4 \cdot 7H_2O$ | 1.1-2.2 | 0.25-0.5 |
| $Na_2SeO_3$ | 0.11-0.22 | 0.05-0.1 |
| $CrCl_2 \cdot 6H_2O$ | 0.1-1.0 | 0.0195-0.195 |
| $CuSO_4 \cdot 5H_2O$ | 0.1-1.0 | 0.025-0.25 |
| $MnSO_4 \cdot H_2O$ | 0.1-1.0 | 0.032-0.32 |

Example 1

Magnesium salts, such as magnesium sulfate ($MgSO_4$) or magnesium chloride ($MgCl_2$) have been used as essential nutrients in the growth media for all microorganisms. They have not, however, been used in high concentrations to grow fungi.

In this experiment, the natural magnesium concentration in a media formulation of the corn, wheat bran and soybean hulls was 50-80 mg/L as magnesium element (Mg). With the additional $MgCl_2 \cdot 6H_2O$, the Mg level increased to 0.33 to 0.58 g/L, a 4 to 7 times increase, respectively. The results show (Table 4) that the Mg in *A. oryzae* increased significantly to as high as 28.3 mg/g (or 28300 ppm) of dry biomass. All results are the average of 4 replicates. As compared with the level of Mg bound to yeast (Table 4), the Mg in yeast only reached 3.5-8.51 mg Mg/g with up to 1250 mg/L Mg added to the YPD (Yeast Extract-Peptone-Dextrose) broth. Therefore based on the above results, the utilization of Mg by *A. oryzae* was nearly 10 times more efficient as compared to yeast.

TABLE 4

Mg Content in *A. oryzae* Biomass when grown in a Mg enriched environment.

| Mg (mg/L) | Mg in *A. oryzae* biomass (mg/g) | Mg Uptake by *A. oryzae* (%) |
|---|---|---|
| 50-80[1] | 2.5-3.4 | >80 |
| 250[2] | 15.8 | 61.6 |
| 500[2] | 28.3 | 49.5 |
| Yeast, 1250[3] | 8.51 | NA |

[1]Natural Mg content in raw agricultural materials varies from batch to batch
[2]Additional Mg as in $MgCl_2 \cdot 6H_2O$ added during the fermentation
[3]Adopted from Duszkiewicz-Reinhard W. et al. 2005. Studies into *Saccharomyces cerevisiae* baker's yeast capacity for binding magnesium under batch conditions. Pol. J. Food Nutr Sci 14(55) No 3: 249-255.

Based on the National Institutes of Health (NIH), Office of Dietary Supplements, the Mg content in the *A. oryzae* biomass produced from a Mg enriched growth environment was higher than all other natural food sources, on an equal weight basis. For example, less than 3 milligrams per day (about 2 Centrum® size tablets) would provide Mg equivalent to one serving of the Mg rich food (Table 5).

TABLE 5

Comparison of Mg content in *A. oryzae* products to selected foods

| Product | Weight (g) | Common Serving | Mg per Serving (mg) | Percent Daily Value |
|---|---|---|---|---|
| Almonds | 28 | 1 oz | 80 | 20 |
| Peanuts | 28 | 1 oz | 60 | 16 |
| Black Beans, cooked | 88 | ½ cup | 60 | 16 |
| Coffee, espresso | 60 | 2 oz | 48 | 12 |
| Whole Wheat Bread | 28 | 1 slice | 23 | 6 |
| Swiss Chard | 175 | ½ cup | 75 | 19 |
| Mg *A. oryzae* | 2.8 | 2 tablets | 80 | 20 |

Example 2

The individually Zn enriched *A. oryzae* allows the product to be precisely formulated into either a multi-mineral supplement or different foods. For example, elderly males may not need an iron (Fe) supplement but may need Zn enhanced food. Both *A. oryzae* and *A. niger* have shown an impressive ability to incorporate Zn into their cell structure to form an organic Zn rich biomass. In Table 6, Zinc sulfate ($ZnSO_4 \cdot 7H_2O$) was used as an inorganic salt to enrich the growth media for *A. oryzae*. The utilization of Zn by *A. oryzae* was highly efficient with 91% of Zn taken up in the media at 250 mg/L and gradually reduced to 35%. The Zn content in the biomass steady increased to 39.6 mg/g (or 39600 ppm) a level that is nearly twice the Zn content compared to Zn in *A. oryzae* with the presence of iron. The report by Stehlik-Tomas (Stehlik-Tomas, V. et al. 2004. Zinc, copper and manganese enrichment in yeast *Saccharomyces cerevisae*. Food Technol. Biotechnol. 42(2):115-120) on Zn in yeast confirmed that the highest amount of Zn in *Saccharomyces cerevisae* was only 0.7 mg/g.

TABLE 6

Zn content in *A. oryzae* biomass when grown in Zn enriched environment

| Zn (mg/L) | Zn in *A. oryzae* biomass (mg/g) | Zn Uptake by *A. oryzae* (%) |
|---|---|---|
| <10[1] | 0.08 | not measured |
| 250[2] | 12.7 | 91 |
| 500[2] | 25.8 | 67 |
| 1000[2] | 38.0 | 48 |
| 1500[2] | 39.6 | 35 |

[1]Natural Zn content in a corn, wheat bran, soybean hull etc formulated media;
[2]Additional Zn as in $ZnSO_4 \cdot 7H_2O$ added during the fermentation.

Based on the National Institute of Health (NIH), Office of Dietary Supplements, the Zn content in the *A. oryzae* biomass produced from a Zn enriched growth environment was much higher than all other natural food sources, on an equal weight basis. For example, 0.27 grams per day (a baby aspirin size tablet) would provide Zn equivalent to 100% of the daily value requirements.

TABLE 7

Comparison of Zn content in *A. oryzae* products to selected foods

| Food | Weight (g) | Common Serving | Zn per Serving (mg) | Daily Value (%) |
| --- | --- | --- | --- | --- |
| Oysters, cooked | 84 | 3 oz | 74 | 493 |
| Beef chuck roast | 84 | 3 oz | 7.0 | 47 |
| Almonds | 28 | 1 oz | 0.9 | 6 |
| Kidney beans, cooked | 150 | ½ cup | 0.9 | 6 |
| Milk, low fat | 300 | 1 cup | 1.0 | 7 |
| Green peas cooked | 175 | ½ cup | 0.5 | 3 |
| Zn *A. oryzae* | 0.27 | <1 tablet | 11 | 100 |

Example 3

Like Zn, selenium (Se) can be co-fermented with or without the presence of iron to produce Se enriched *A. oryzae* biomass. But in this example, when Se in the form of sodium selenite solution of 0.1% was added during the fermentation of *A. oryzae* without the iron, the Se content in the fungal biomass increased from 0.4 mg/g (400 ppm) to as much as 3.36 mg/g (3360 ppm) (Table 8). As the daily recommended dose of Se is very low, it is preferred to produce a Se enriched product on a stand-alone basis to avoid either over-dosing on Se, or under-dosing on Fe. As compared with selected foods, *A. oryzae* with Se has a relatively high Se concentration; 0.02 grams per day could deliver 100% of the daily value (DV).

TABLE 8

Se content in *A. oryzae* biomass when grown in a Se enriched environment

| Se (mg/L) | Se in *A. oryzae* biomass (mg/g) | Se Uptake by *A. oryzae* (%) |
| --- | --- | --- |
| 50 | 2.37 (2370 μg/g) | 59 |
| 100 | 3.36 (3360 μg/g) | 43 |

TABLE 9

Comparison of Se content in *A. oryzae* products to selected foods

| Description | Weight (g) | Common Serving | Se per Serving (μg) | Percent Daily Value |
| --- | --- | --- | --- | --- |
| Brazil nut | 28 | 1 oz | 544 | 777 |
| Ham, roasted | 84 | 3 oz | 40 | 60 |
| Brown rice, cooked | 300 | 1 cup | 19 | 27 |
| Whole wheat bread | | 1 slice | 0.9 | 6 |
| Lentils, boiled | 300 | 1 cup | 6 | 9 |
| Milk, 1% | 300 | 1 cup | 8 | 11 |
| Se *A. oryzae* | 0.02 | | 55 | 100 |

Example 4

When the fungal fermentation was conducted with a single mineral, chromium, copper or manganese salt, the mineral content in fungal mycelia was significantly enhanced (Table 10). In all examples, the natural fungal minerals were highly concentrated and would provide an economic alternative to the inorganic salt and synthetic mineral chelates.

TABLE 10

Cr, Cu or Mn in *A. oryzae* when grown in the mineral enriched environment.

| | Mineral content in A.o., ppm | Amount of A.o. to Meet 100% DRI in average adult, g | Number of Dose per Kg of A.o. Product |
| --- | --- | --- | --- |
| Chromium | 8000 | 0.0000034 | 228,571 |
| Copper | 17400 | 0.000057 | 17,400 |
| Manganese | 20700 | 0.000097 | 10,350 |

Example 5

Currently, human mineral supplementation is likely to be in a multi-mineral and vitamin form, formulated with each individual component. A similar approach is used in food fortification, for example, in breakfast cereals. The advantage of such an approach is that the dosage of each mineral and vitamin can be precisely controlled according to Daily Value (DV) recommended by the US Food and Drug Administration. However, it is likely that when multi minerals are consumed together, the absorption of one may interfere with the others. For example, the interaction between Fe and Zn, Zn and Copper (Cu), etc. Previous researchers have also shown an interaction among minerals with phytate in plant based diets. The use of *A. oryzae* bonded minerals to formulate a multi-mineral supplement may contain less mineral interactions as each mineral has already bonded to the cell wall and protein of *A. oryzae*. The slow release feature of the *A. oryzae* bonded minerals may also reduce the interaction among minerals.

To produce a natural *A. oryzae* with enhanced multi-minerals has been found to be practical. Such a product may not meet the DV, for example, DV of magnesium is 400 mg, requirement in a single dose, but could provide enhanced multi-minerals on a daily basis. The concentration of each mineral in such a product can be adjusted during the fermentation to create different desired combinations. Table 11 demonstrates that with a selected growth media formulation, the result is a multi-mineral, Fe, Zn, Cr, Se, Cu and Mn enhanced biomass in only a 0.5 g dose. The concentration of each mineral can be in the range of plus/minus four times multiple. The types of minerals are not limited to the minerals in Table 11. This example not only demonstrates the ability of *A. oryzae* to uptake high concentrations of each mineral, but also shows the uptake of the multi-trace minerals in a natural balanced way as indicated by different uptake preferences.

TABLE 11

A multi-mineral approach to create an *A. oryzae* biomass-based all trace natural mineral supplements, in a 0.5 gram Dose.

| Mineral | Mineral content in *A. oryzae* biomass mg/Kg | Mineral uptake by *A. oryzae*, % | % DRI per Dose |
| --- | --- | --- | --- |
| Zn | 24100 | 100 | 110 |
| Mg | 10000 | 5 | 2 |
| Se | 70 | 64 | 64 |
| Cr | 104 | 100 | 150 |
| Cu | 1240 | 100 | 31 |
| Mn | 1720 | 100 | 43 |

Two large industrial trials have been undertaken with fermentation volume of 2000 L each without any production difficulties. As the size of fermentation vessels increase, the ability to manage and control issues like airflow improved. Both trials confirmed that a fungal biomass could be produced containing enhanced levels of zinc, magnesium, selenium, chromium, copper, manganese or combinations thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for forming a nutritional supplement containing minerals, the process comprising:
   providing a culture medium formulated with an agricultural by-product or a food processing by-product;
   providing inorganic salts of zinc, magnesium, selenium, chromium, copper, and manganese to the culture medium, wherein the salts are added at a concentration of at least about 5 mg of inorganic salt per liter of culture medium;
   culturing filamentous fungi selected from *Aspergillus oryzae* or *Aspergillus niger* in the culture medium to accumulate the minerals zinc, magnesium, selenium, chromium, copper, and manganese in the filamentous fungi in organic form in a single culture; and
   harvesting the filamentous fungi from the single culture to obtain a nutritional supplement containing the minerals comprising fungal biomass having the minerals zinc, magnesium, selenium, chromium, copper, and manganese in organic form;
   wherein at the minerals are present from 1 to 60000 mg/kg in the fungal biomass; and
   wherein the nutritional supplement does not contain raised levels of iron from the fungi, the levels being less than 200 mg/kg.

2. The process according to claim 1, wherein the agricultural by-product comprises waste derived from agriculture production of corn, wheat, sugar beet, cane sugar, soybean, or whey.

3. The process according to claim 2, wherein the agricultural by-product is selected from the group consisting of sugar cane and beet pulps, soybean hull, soybean process whey, wheat hull, corn steeping liquid, and soybean whey.

4. The process according to claim 1, wherein the food processing by-product is selected from the group consisting of corn steeping liquor, soybean whey, sugar cane and beet molasses, soybean hull and wheat bran, and wheat hull.

5. The process according to claim 1, wherein the salts are added at the concentration of 50 to 1500 mg of salt per liter of culture medium.

6. The process according to claim 1, wherein culturing of the filamentous fungi is carried out at a temperature between 25° C. and 35° C.

7. The process according to claim 1, wherein the harvesting is by filtration, filter press, belt press, centrifugation, or drying.

8. The process according to claim 7, wherein the drying is carried out by rotary drier, steam drier or vacuum drier.

9. The process according to claim 7, wherein the drying is carried out at a temperature lower than about 95° C.

10. The process according to claim 1, wherein the zinc is in the range of 10 to 60000 mg/kg, magnesium is in the range of 10 to 60000 mg/k, selenium is in the range of 1 to 4000 mg/kg, chromium is in the range of 4 to 8000 mg/kg, copper is in the range of about 60 to 20000 mg/kg, and manganese in the range of 60 to 20000 mg/kg.

11. The process according to claim 1, wherein the nutritional supplement containing minerals has levels of iron less than 200 mg/kg.

12. The process according to claim 10, wherein the nutritional supplement containing minerals is formulated as tablets, capsules, caplets, powders, granules, ampoules, vials, ready-to-use solutions or suspensions, drinks, or lyophilized materials.

13. The process according to claim 1, further comprising formulating the nutritional supplement containing minerals for oral delivery.

* * * * *